United States Patent [19]

Hawks

[11] 4,291,917
[45] Sep. 29, 1981

[54] LOW PRESSURE INFANT SEAT FOR NORMALLY SEATING INFANTS WITH MENINGOMYELOCELE OR OTHER SENSITIVE BACK DEFORMITIES

[76] Inventor: Gail B. Hawks, 4615A Walden Pond Dr., Raleigh, N.C. 27604

[21] Appl. No.: 77,117

[22] Filed: Sep. 19, 1979

[51] Int. Cl.³ ............................................. A47D 13/02
[52] U.S. Cl. .................................... 297/452; 297/460
[58] Field of Search ............... 297/460, 452, 453, 457, 297/477, 377

[56] References Cited

U.S. PATENT DOCUMENTS

| | | | |
|---|---|---|---|
| 2,547,350 | 4/1951 | Veale | 297/453 |
| 3,101,972 | 8/1963 | Laughlin | 297/377 |
| 3,197,255 | 7/1965 | Caudill | 297/460 |
| 3,528,701 | 9/1970 | Laughlin | 297/377 |
| 3,669,497 | 6/1972 | Massonnet | 297/460 |
| 3,669,498 | 6/1972 | Meyers et al. | 297/460 |
| 3,949,435 | 4/1976 | Dionne | 297/439 |
| 4,062,590 | 12/1977 | Polsky et al. | 297/457 |
| 4,072,345 | 2/1978 | Matsuda | 297/452 |

Primary Examiner—Francis K. Zugel
Attorney, Agent, or Firm—William C. Lawton

[57] ABSTRACT

The present invention relates to an infant seat that is particularly adapted to be used for infants with the condition known as spina bifida (open spine), with attention to the related meningocele or meningomyelocele. The infant seat is comprised of a device molded to allow the infant to be maintained in a sitting or supine position without pressure to the above mentioned defect. The lower porton of the device is composed of an open area generally in the shape of a square, across which a detachable mesh insert can be stretched and secured to snaps. Safety straps for securing the infant in the seat are utilized. An adjustable bracing device is attached to the back of the seat for the purpose of adjusting to and maintaining various positions.

4 Claims, 1 Drawing Figure

LOW PRESSURE INFANT SEAT FOR NORMALLY SEATING INFANTS WITH MENINGOMYELOCELE OR OTHER SENSITIVE BACK DEFORMITIES

The present invention relates to orthopedic devices, and more particularly to a low pressure infant seat adapted to be utilized for normally seating infants with meningomyelocele or other sensitive back deformities.

BACKGROUND OF THE INVENTION

Infant seats have been used in the past for the purpose of transporting and/or maintaining infants in sitting positions or lying on their backs. For example, see the disclosures found in U.S. Pat. Nos. 3,320,949, 3,747,759, 3,834,759, 3,949,435, 3,974,827, 3,992,056.

Infants who are born with the condition of spina bifida with the associated meningocele or menimgomyelocele are not able to tolerate pressure on these areas, and are therefore restricted in respect to positions of comfort. Generally, these infants must be cared for while lying on their sides or stomachs. These positions do not generally avail themselves to transportation or care of the infant in a regular infant seat.

There is a real need for a device which would enable the infant to maintain a sitting position or a supine position without pressure to the area of the meningocele/meningomyelocele. Spina Bifida occurs in three out of every one thousand babies born in the U.S. Eleven thousand children are born with this defect annually, making it the second largest major birth defect in the country.

SUMMARY OF INVENTION

The present invention presents an infant seat that is adapted to accommodate an infant with the condition of spina bifida and associated meningocele/meningomyelocele. Meningocele refers to the protrusion of membranes which normally cover the spinal cord through an opening in the spinal cord, forming a cyst filled with fluid and covered with skin. Meningomyelocele refers to the protrusion of both the membranes and the spinal cord through the defect, again being covered by a thin membrane of skin.

The infant seat generally comprises a device molded so as to form a seat with a back which extends beyond the head area for the purpose of support. An adjustable bracing device attached to the back of the seat allows for adjustment to and maintenance of one of several desired positions by manipulating the degree of extention of the bracing device. The bracing device may be formed so as to extend from four bracing points on the dorsal side of the seat to allow for adjustment of the seat to various positions and maintenance of the seat in those positions. An open area is provided in the lower portion of the said infant seat beginning at the base of the back portion in the vicinity of the juncture of said back portion with the rear of the seat portion. This open area extends up the back portion a sufficient distance to prevent pressure to the meningocele, the meningomyelocele or the surrounding area. A detachable mesh insert applied to the lower portion of the back of the seat allows the infant to maintain a position on his back without pressure to the area of the meningocele or meningomyelocele. The detachable mesh is applied across the said opening and the means provided for removably attaching said mesh across said opening are positioned so as to prevent pressure points at or near the spinal area at the upper edge of the mesh. The mesh is a resilient material which can be stretched across the open lower back portion. One type of means for detachably attaching the mesh to the infant seat includes using snaps where one portion of the snap is attached to the infant seat around the said opening and the mating portion of the snap is attached to the said mesh. The said mesh may be in a generally rectangular shape to be stretched across the said lower portion of the seat. The seat may also have side edges as shown in the drawing. Safety straps which are attached to the seat laterally and anteriorally are intended to prevent the infant's dislocation from the seat. There may be three such safety straps, attached laterally and proximately to the seat, for purposes of maintaining the infant in position while situated in the seat.

Figure 1:
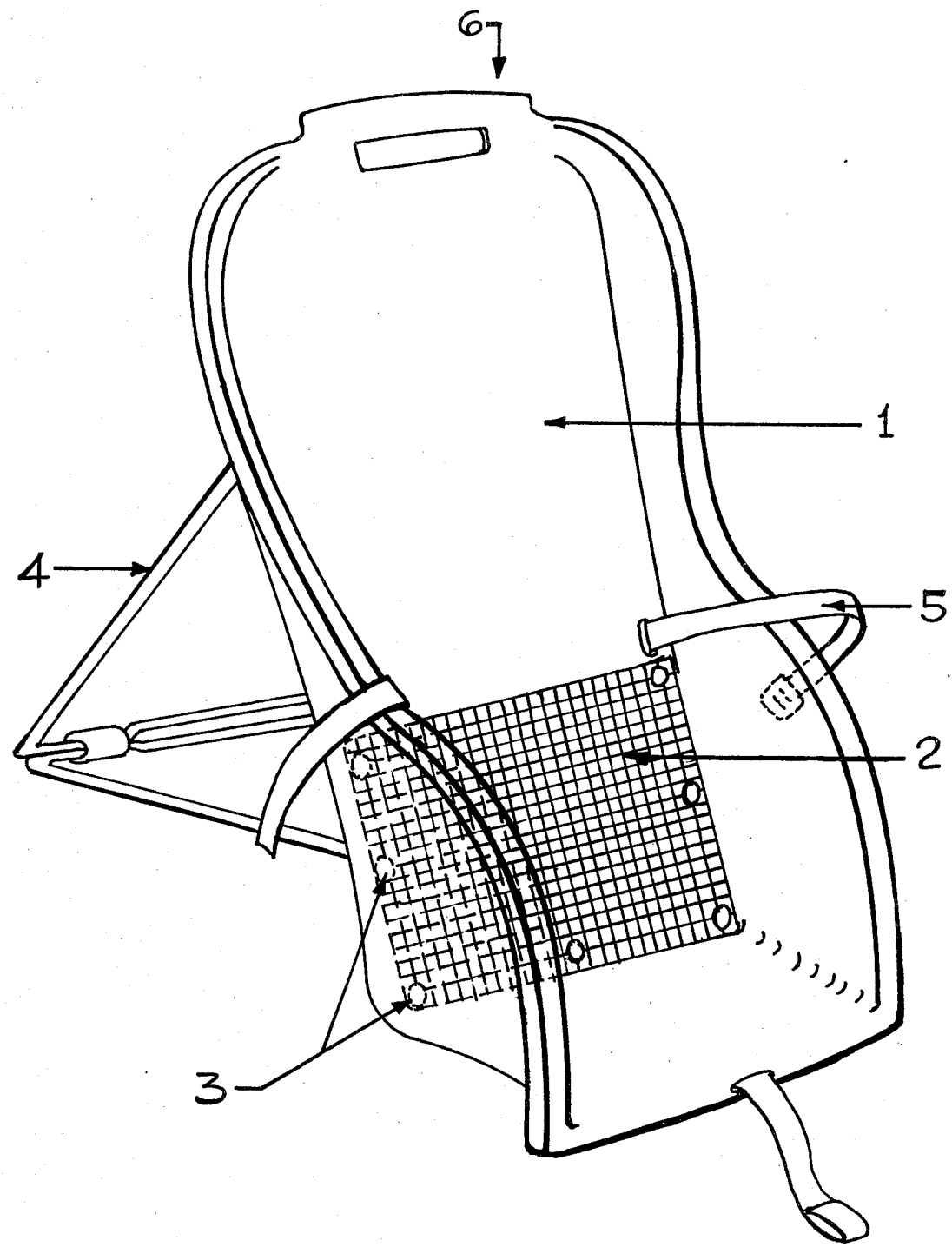
FIG. 1 is a perspective view of the orthopedic low pressure infant seat of the present invention.

THE LOW PRESSURE INFANT SEAT FOR NORMALLY SEATING INFANTS WITH MENINGOMYELOCELE OR OTHER SENSITIVE BACK DEFORMITIES

With further reference to the drawing, a low pressure infant seat, indicated generally by the numeral 6, is shown therein and includes a generally planar backrest curved at the bottom so as to form a seat, indicated generally by the numeral 1.

Numeral 2 generally refers to a detachable mesh insert, constructed of cotton or synthetic fiber, rectangular in shape.

Numeral 3 refers to snapping devices, permanently secured to the backrest, for the purpose of securing the detachable mesh insert into place. (Correspondants to the snapping device are, of course, secured to the bottom of the detachable mesh insert.)

Numeral 4 refers to the adjustable bracing device, constructed of a strong metal, attached to the back of the seat at 4 points to allow for adjustment to and maintenance of one of several desired positions by manipulating the degree of extension of the bracing device.

Numeral 5 refers to the safety straps, constructed of leather or plastic, which are attached to the seat laterally and anteriorally and intended to prevent the infant's dislocation from the seat.

It is important to realize that with the low pressure infant seat 6 of the present invention that infants with lower back deformities will be able to sit normally to be fed and interacted with by others, without undue pressure to the affected area.

It represents a new and useful orthopedic device which is relatively simple and inexpensive.

The present invention, of course, may be carried out in other specific ways than those herein set forth without departing from the spirit and essential characteristics of the invention. The present embodiments are, therefore, to be considered in all respects as illustrative and not restrictive, and all changes coming within the meaning and equivalency range of the appended claims are intended to be embraced therein.

What is claimed is:

1. A low pressure infant seat for normally seating infants with meningocele/meningomyelocele or other sensitive back deformities comprising a device molded so as to form a seat having a seat portion with a back portion extending from the rear of the seat portion beyond the head area for the purpose of support, said device having an open area provided in the lower portion of the back of the said device beginning at the base of the back portion in the vicinity of the juncture of said back portion with the rear of the said seat portion and extending up the back portion a sufficient distance to prevent a pressure to the meningocele/meningomyelocele or the surrounding area; a detachable mesh insert applied over the said open area in the said lower portion of the back of the said device; means which allow for attaching and detaching the said mesh insert to the said device, said means so positioned so that no pressure points are formed at or near the spinal area at the upper edge of the said mesh; an adjustable bracing device attached to the back of the said device; safety straps for maintaining an infant in position in the device; wherein said device has side portions extending forwardly, wherein said detachable mesh insert includes a generally rectangular portion of resilient material stretched across the said open area, wherein said means which allow for attaching and detaching said mesh insert are detachable fasteners connected to the back portion and mesh insert and are positioned around the open area, wherein said bracing device extends from four points on the dorsal side of the said device to allow for adjustment of position of said device, and wherein said safety straps are attached laterally and proximate to the said device.

2. The low pressure infant seat of claim 1 wherein said means which allow for attaching and detaching said mesh insert consist of seven snaps situated around said open area.

3. The low pressure infant seat of claim 1 wherein said adjustable bracing device is attached at four points on the dorsal side of the said device to allow for the adjustment to and maintenance of various positions.

4. The low pressure infant seat of claim 1 wherein there are three said safety straps attached laterally and proximately to the said device.

* * * * *